US00PP31790P2

(12) United States Plant Patent
Bédard

(10) Patent No.: US PP31,790 P2
(45) Date of Patent: May 26, 2020

(54) SHRUB ROSE PLANT NAMED 'WEKCHEDOWAHOR'

(50) Latin Name: *Rosa hybrida*
Varietal Denomination: WEKchedowahor

(71) Applicant: Gardens Alive! Inc., Greendale, IN (US)

(72) Inventor: Christian Bédard, Rancho Cucamonga, CA (US)

(73) Assignee: Gardens Alive! Inc., Greendale, IN (US)

( * ) Notice: Subject to any disclaimer, the term of this patent is extended or adjusted under 35 U.S.C. 154(b) by 0 days.

(21) Appl. No.: 16/501,754

(22) Filed: Jun. 3, 2019

(51) Int. Cl.
*A01H 5/02* (2018.01)
*A01H 6/74* (2018.01)

(52) U.S. Cl.
USPC ..... Plt./104

(58) Field of Classification Search
USPC ..... Plt./101, 102, 104
See application file for complete search history.

*Primary Examiner* — Susan McCormick Ewoldt
(74) *Attorney, Agent, or Firm* — Barbara Campbell; Cochran Freund & Young LLC

(57) ABSTRACT

A new and distinct variety of shrub rose having a compact, bushy, upright growth habit, suitable for outdoor garden decoration and yellow flowers, is disclosed.

1 Drawing Sheet

Genus and species: *Rosa hybrida.*
Denomination: 'WEKchedowahor'.

BACKGROUND

'WEKchedowahor' is a new and distinct variety of shrub rose. 'WEKchedowahor' originated from a controlled hybridization in April to June 2012 in Pomona, Calif. between the female parent, an un-named and unpatented cross between 'CHRiscinn' (unpatented) and 'HARpageant' (U.S. Plant Pat. No. 22,587), and the male parent, 'WEKsolcibarko' (U.S. Plant Pat. No. 28,656).

The resulting seeds from the hybridization were planted and evaluated. 'WEKchedowahor' was selected between March to July 2013 in Pomona, Calif. 'WEKchedowahor' was first asexually propagated in July 2013 in Wasco, Calif. on its own root cuttings and subsequently by budding and grafting on the plant/rootstock of *Rosa hybrida* 'Dr. Huey' (unpatented).

Other subsequent asexual propagations were conducted in controlled environments in Pomona, Calif. and Tipp City, Ohio and demonstrate that 'WEKchedowahor' reproduces true to type in successive generations of asexual reproduction via softwood cuttings, budding, and grafting.

SUMMARY

The following are the most outstanding and distinguishing characteristics of this new variety when grown under normal horticultural practices in Pomona, Calif. and Tipp City, Ohio.

1. A shrub rose having a compact, bushy, upright growth habit, suitable for outdoor garden decoration; and
2. Yellow flowers.

DESCRIPTION OF THE PHOTOGRAPH

This rose plant is illustrated by the accompanying photograph which shows the individual parts of the plant. The colors shown are as true as can be reasonably obtained by conventional photographic procedures. The photograph is of the parts of a 3 to 4-year old rose plant grown outdoors in Tipp City, Ohio in August 2018. The colors shown are as true as can be reasonably obtained by conventional photographic procedures.

The photograph shows from top to bottom, starting at the top (first) row, three individual flowers in full bloom; the second row shows from left to right a flower in mid-bloom, a flower just opening, and the flower bud, pedicel and sepals; the third row shows from left to right, the lower surface of compound leaf, the upper surface of the compound leaf, and the reproductive parts of the flower with the petals removed; the fourth row show the stem, foliage and bud of a flowering branch; and the fifth (bottom) row shows an individual stem with only thorns of the plant.

DETAILED DESCRIPTION

The following detailed descriptions set for the distinctive characteristics of 'WEKchedowahor'. The data which define these characteristics were collected from asexual reproductions carried outdoors in Tipp City, Ohio in August 2018. The phenotype of this new variety will vary somewhat with variation in environmental, climatic, and cultural conditions as it has not been tested in other environments. Color references are to The R.H.S. Colour Chart of The Royal Horticultural Society of London (R.H.S.) 2001.

Classification:

*Family.*—Rosaceae.
*Species.*—*Rosa hybrida.*
*Common name.*—Shrub rose.
*Variety.*—'WEKchedowahor'.

Parentage:

*Female parent.*—Un-named rose plant (unpatented).
*Male parent.*—'WEKsolcibarko' (U.S. Plant Pat. No. 28,656).

Growth: The plant has a bushy upright medium height growth habit, about 120 to about 140 cm in height and about 90 to about 120 cm spread at the widest point, with full branching. 'WEKchedowahor' displays vigorous growth and the canes are of medium to caliper for the class, about 0.7 cm to about 1.1 cm in diameter at the widest point.

Stems: The color of the major stems is near between RHS 138A. The major stems are rough in texture and they bear several large prickles that are about 1.0 cm to about 1.1 cm in length. The large prickles are hooked downward with a medium length base; prickle color is near RHS 146D. The major stem bears several prickles of similar shape and coloration and which are near RHS 146D in color. There are no hairs that have been observed on stems. The color of the branches is near RHS 138A. The branches are rough in texture and bear several prickles which are of similar size and shape to the large prickles on the major stems; prickle color is near RHS 146D. The branches bear no small prickles. There are no hairs that have been observed on branches. The color of the new shoots is near 146D. The new shoots are rough in texture and they bear several large prickles which are of similar size and shape to the large prickles on the major stems; prickle color is near RHS 147D. The shoots bear no small prickles. There are no hairs present on new shoots.

Foliage: The compound leaves are usually comprised of three to five to seven leaflets and are borne abundantly. The five-leaflet leaves are about 11 cm to about 12 cm in length and about 7.5 cm to about 8 cm in width at the widest point, leathery in texture on both sides, and semi-glossy in finish on the upper side and matte the under-side. The leaves have a pinnate venation pattern. The terminal leaflets are about 4.5 to about 5 cm in length and about 3.5 cm to about 4 cm in width at the widest point, shaped ovate with acute to subacute apices and somewhat round bases. Their margins are doubly serrate. The upper surface color of the mature leaf is near RHS 136A. The lower surface color of the mature leaf is near RHS 138B. The under and upper colors of the leaf veins on the mature leaf are similar in coloration to the upper and under surfaces colors of the mature leaf. The upper surface color of the young leaf is near RHS 146C, lightly suffused with between RHS 178A and RHS 178B. The lower surface color of the young leaf is near RHS 178B. The lower and upper surface colors of the leaf veins on the young leaf are similar in coloration to the upper and under surfaces colors of the young leaf. The rachis is about 4.5 cm to about 5.5 cm in length, about 1.5 mm to about 1.9 mm in width at the widest point, and somewhat rough. The upper surface is shallowly grooved with a few stipitate glands on the edges of the grooves. The lower surface of the rachis is somewhat rough with some stipitate glands and small prickles. The rachis color is near RHS 138B on the lower surface and near RHS 136A on the upper surface, sometimes lightly suffused on the young leaves with near RHS 178B. The stipules are about 0.9 cm to about 1.1 cm in length and of medium width, about 4 mm to about 6 mm, with medium straight points that usually turn out at an angle of less than 45 degrees. The lower and upper surface color of the stipule is near RHS 138B. The upper and lower surfaces of the stipules are smooth in texture. The petiole average in caliper and smooth. The upper surface is shallowly grooved with very few stipitate glands on the edges of the grooves. The lower surface of the petiole is smooth. The petiole is about 1.0 mm to about 1.3 mm in length and about 1 mm in width at the widest point. The petiole color is near RHS 136A on the lower surface and near RHS 138B on the lower side, lightly suffused on the young leaves with RHS 178B.

Flower: 'WEKchedowahor' usually bears its flowers singly and sometimes, in clusters of two to three per stem. Flowers are borne on strong medium to long stems, about 40 cm to about 60 cm. The occasional cluster ranges from about 7 cm to about 9 cm in diameter before the flowers begin to open. Outdoors, the plant blooms abundantly and nearly continuously during the growing season. The flowers have a slight apple-like fragrance. The receptacle of the flower is medium in length, about 7 mm to about 9 mm, and average in caliper, about 5 mm to about 6 mm in diameter. The receptacle is funnel shaped in form. Its surface is smooth with very moderately thick dry fleshy walls. The receptacle color is near RHS 146B.

Flower bud: Before the calyx breaks, the bud is about 2 cm to about 2.1 cm in diameter at the widest point, about 2.5 cm to about 2.7 cm in length and pointed to ovoid in shape with a conspicuous neck. The surface of the bud bears between 7 to 10 foliaceous appendages, usually with foliaceous parts extending beyond the tip of the bud about one-quarter or more of its length. Bud color is near RHS 146B before the calyx breaks. As the petals open, after the calyx breaks, the bud is about 2.2 cm to about 2.4 cm in diameter at the widest point, about 2.5 cm to about 2.7 cm in length, and pointed to ovoid in form.

Petals and petaloids: The color of the lower and upper surfaces of the newly opened petals is near between RHS 5B and RHS 5C. At the point where the petal attaches, there is a very small zone of near RHS 5A. The color of the upper surfaces of the newly opened flower is between RHS 5B and 5RHS C. At the point where the petal attaches, there is a very small zone near RHS 5A. The substance of the petals is leathery and of medium thickness, with upper surfaces moderately shiny to satiny and the under surfaces satiny. The petals are about 3.5 cm to about 4.0 cm in length and about 3.5 cm to about 4.3 cm in width at the widest point. Petal margins are entire. The outer petals are orbicular in shape with apices rounded. The inner petals are obovate in shape with apices obtuse Petaloids are about 1 cm to about 2.3 cm in length and about 0.6 cm to about 1.1 cm in width at the widest point. Petaloids are shaped oblanceolate to spatulate with rounded to obtuse apices.

Sepals: The sepals are 5 per flower, about 2.2 cm to about 2.5 cm in length and about 0.7 cm to about 1.1 cm in width at the widest point. The outer surface color of the sepal is near RHS 146B. The outer surface of the sepal is smooth rough and bears between 3 to 5 foliaceous appendages with numerous fine hairs. The inner surface color of the sepal is near RHS 138B bordered by near RHS 138D. After the sepals open, the inner surface color is sometimes lightly suffused, especially on the area exposed to the sun, with between RHS 178C to RHS 178D. The inner surface of the sepal is covered fine wooly tomentum; sepal margins are entire and lined with many hairs and stipulate glands. The sepals are very permanent, spear-shaped and recurved with acute apices.

Peduncle: The peduncle is about 8 cm to about 9 cm in length of average caliper, about 3.5 mm to about 4.5 mm in diameter, and erect and stiff. It is smooth with several stipitate glands. The peduncle color is near RHS 146B.

Newly open flower: The lower and upper surface color of the outer petals is near between RHS 5B and RHS 5C. At the point where the petal attaches, there is a very small zone of near RHS 5A. The upper surface color of the outer petals is near between RHS 5B and RHS 5C. At the point where the petal attaches, there is a moderately somewhat very small large zone of near RHS 5A. The lower and upper surface color of the intermediate petals is between RHS 5B and RHS 5C. The upper surface color of the intermediate petals is between RHS 5B and RHS 5C. The lower and upper surface color of the inner petals is between RHS 5B and RHS 5C. The upper surface color of the inner petals is between RHS 5B and RHS 5C. The lower and upper surface colors of the petaloids are similar in coloration to the upper and lower surfaces of the intermediate and inner petals. The general tonality of the newly opened flower is between RHS 5B and RHS 5C.

Three-day-old flower: The lower and upper surface color of the outer petals is near between RHS 5C and RHS 5D. At the point where the petal attaches, there is a very small zone of near RHS 5A. The upper surface color of the outer petals is between RHS 5B and RHS 5C. At the point where the petal attaches, there is a very small zone of near RHS 5A. The lower and upper surface color of the inner petals is between RHS 5C and RHS 5D. The upper surface color of the inner petals is between RHS 5C and RHS 5D. The lower and upper surface colors of the petaloids are similar in coloration to the upper and under surfaces of the intermediate and inner petals. The general tonality of the three-day-old flower is between RHS 5C and RHS 5D. On the spent bloom, the petals usually drop off cleanly. In August in Tipp City, Ohio blooms on the bush growing outdoors generally last about four to five days. Cut roses from plants grown outdoors and kept at normal indoor living temperatures generally last about five to six days.

Fully-open flower: When fully open, the bloom ranges from about 9 cm to about 10.5 cm in diameter. Petalage is very double with about 50 to 55 petals and about 10 to 15 petaloids irregularly arranged. When partially open, the bloom form is high centered to globular, and the petals are spiraled and petal edges reflexed inward. When fully open, the bloom form is full, and the petals are imbricated with petal edges somewhat quilled and reflexed inward.

Hips formation: Hips have not been observed on this variety when grown in Tipp City, Ohio.

Male reproductive organs: Stamens are average in number (average about 45 to 50) and are arranged regularly about the pistils; a few are mixed with petaloids or tucked in the calyx. The filaments are moderately long length, about 6 to about 9 mm, most with anthers. Filaments are near RHS 5C in color. The anthers are medium for the class and all open approximately at the same time. Anther color when immature is near RHS 22A on the external part and near 5B on the internal part. Anther color at maturity is near RHS 163A on the external part and near 163C on the internal part. Pollen is moderate to abundant and near RHS 165C in color.

Female reproductive organs: Pistils vary in number, average about 35. The styles are somewhat even uneven, very moderately short to average to long in length, about 6 mm to about 7 mm, average in caliper, and bunched to columnar. Stigma color is between RHS 158A to RHS 158B. Style color is near RHS 5D with a blush of RHS 60B. Ovaries are enclosed in the calyx. The ovaries are medium size and between RHS 158B and RHS 158C in color.

Disease resistance: The plant displays an average above average degree of resistance to powdery mildew (*Sphaerotheca pannosa*), downy mildew (*Peronospora sparsa*), black spot (*Diplocarpon rosae*) and rust (*Phragmidium* sp.) as compared to other commercial varieties grown under comparable conditions in Tipp City, Ohio. The plant's winter hardiness has been demonstrated to withstand minus 15 degrees F. without snow cover or winter protection. Drought resistance has not been determined.

COMPARISON WITH PARENTAL AND COMMERCIAL LINES

'WEKchedowahor' may be distinguished from the female parent, an un-named seedling, by the following combination of characteristics. 'WEKchedowahor' has more flowers with longer durability than the female parent. 'WEKchedowahor' has less vigorous, more compact growth than the female parent.

'WEKchedowahor' may be distinguished from the male parent, WEKsolcibarko', by the following combination of characteristics. 'WEKchedowahor' has dark red flowers, whereas the male parent has hot-pink colored flowers. 'WEKchedowahor' has medium-sized flowers for a miniature rose, whereas the male parent has large flowers.

When 'WEKchedowahor' is compared to the commercial comparison rose variety 'KORhedani' (U.S. Plant Pat. No. 19,598), the following differences are noted in Table 1.

TABLE 1

| Characteristic | 'WEKchedowahor' | 'KORhedani' |
|---|---|---|
| Petal count | Approximately 75 petals under normal conditions. | Approximately 30 to 32 petals under normal conditions |
| Average number of prickles per 10.0 cm of stem | 25 to 30 large prickles, and upwards of 60 small prickles. | Less than 1 |
| Average open flower diameter | 40.0 mm to 45.0 mm | 55 mm |

I claim:

1. A new and distinct variety of Shrub rose plant named 'WEKchedowahor' as illustrated and described herein.

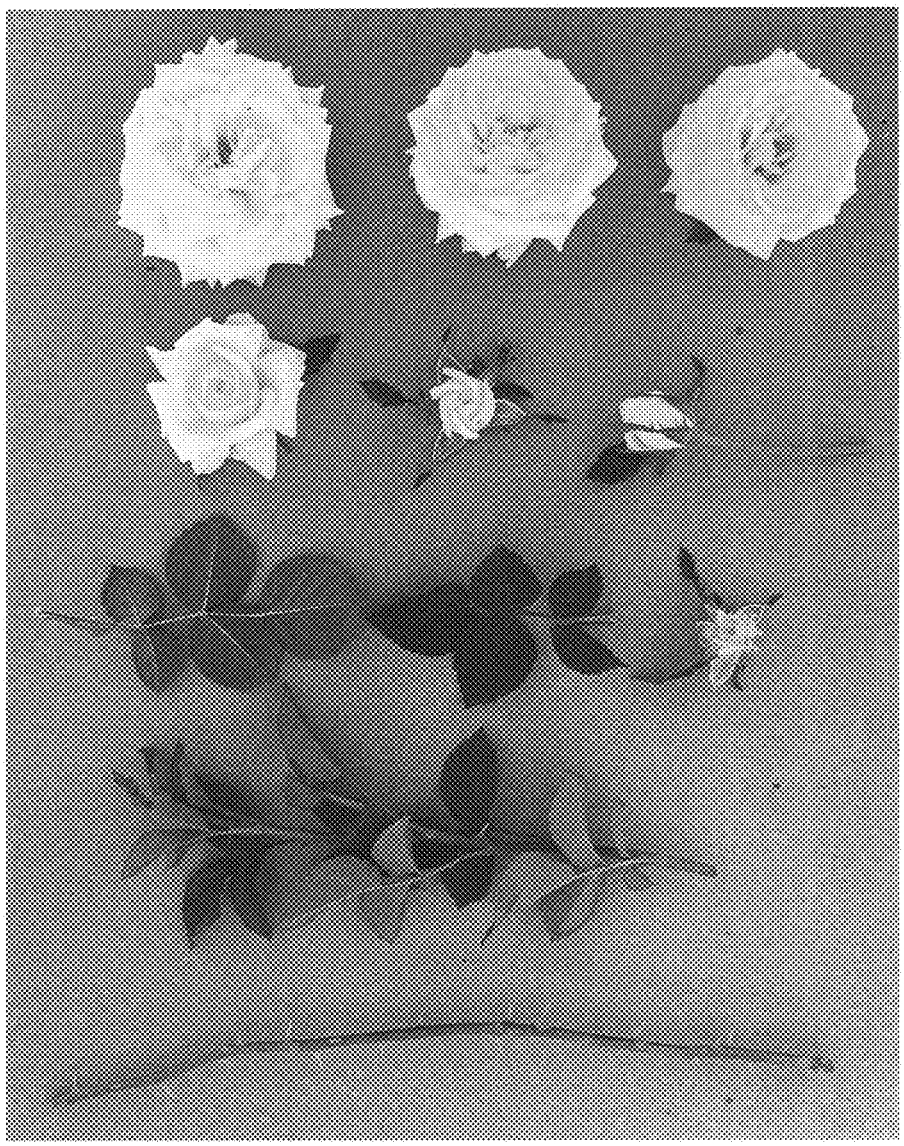

* * * * *